United States Patent [19]

Szucs

[11] 4,312,865
[45] Jan. 26, 1982

[54] MEDICATION HAVING PENETRATION THROUGH CUTANEOUS SURFACES INTO ARTICULAR AND MUSCULAR AREAS

[76] Inventor: Murrill M. Szucs, 50 W. State St., Akron, Ohio 44308

[21] Appl. No.: 166,307

[22] Filed: Jul. 7, 1980

[51] Int. Cl.³ ............................................. A61K 31/56
[52] U.S. Cl. ................................................... 424/243
[58] Field of Search .......................................... 424/243

[56] References Cited

U.S. PATENT DOCUMENTS 4,130,643 12/1973 Smith .................................. 424/243
4,177,267 12/1979 Herschler ........................... 424/243

*Primary Examiner*—Elbert L. Roberts
*Attorney, Agent, or Firm*—Oldham, Oldham, Hudak & Weber Co.

[57] ABSTRACT

A medication that penetrates the surface of the skin is provided. The articular and muscular areas subject to discomfort may be relieved by the topical application of the medication. The medication has a penetrant of dimethyl sulfoxide, an anti-inflammatory agent, made from glucocorticoids, and a topical anesthetic compound. The medication greatly relieves pain and reduces swelling.

14 Claims, No Drawings

MEDICATION HAVING PENETRATION THROUGH CUTANEOUS SURFACES INTO ARTICULAR AND MUSCULAR AREAS

TECHNICAL FIELD

This invention relates to a therapeutic composition for the relief of intra-articular and intra-muscular discomfort and the method for application of that therapeutic composition to cutaneous surfaces.

BACKGROUND ART

Treatment of discomfort in intra-muscular and intra-articular areas has typically involved medications injected beneath the cutaneous surface or oral administration. Use of the blood stream to carry the medication to the discomforted area may sometimes cause undesirable side effects to areas not desired for treatment. Further, the delay of transmission of the medication into the blood stream is not conducive to rapid relief. Injection of medications directly into a joint may cause recrystallization of the medication within the joint, causing synovitis.

A direct penetration of an active ingredient medication involves percutaneous administration of the medication. The use of lower aliphatic sulfoxides in slight concentrations has been recorded in the prior art. The following table indicates those United States patents where the concentration of the lower aliphatic sulfoxide is less than 25 percent.

TABLE 1

3,981,996, 4,148,917, 4,148,874, 3,592,930, 4,148,887, 3,952,099, 3,888,995, 3,896,238, 4,046,886, 4,130,667, 4,148,893, 3,953,599, 4,148,924.

The prior art also discloses compositions where the lower aliphatic sulfoxide comprises greater than 50 percent of the overall composition. Table 2 illustrates the United States patents indicating this majority composition ingredient.

TABLE 2

3,551,554, 3,743,727, 3,771,606, 3,771,602, 3,592,936.

The use of lower aliphatic sulfoxide has been criticized, particularly dimethyl sulfoxide. U.S. Pat. Nos. 3,527,864; 3,903,256; and 3,678,156 all teach the preferred use of higher aliphatic sulfoxides. Indeed, some percutaneous penetrant systems emphasize the avoidance of lower aliphatic sulfoxides, to wit: U.S. Pat. Nos. 4,032,661; 4,070,449; and 3,326,768.

Dimethyl sulfoxide was regarded as an active ingredient in U.S. Pat. Nos. 3,740,420 and 3,790,676. Further, U.S. Pat. No. 3,321,364 teaches the use of dimethyl sulfoxide as a foliage insecticide, while U.S. Pat. No. 3,527,863 teaches the use of dimethyl sulfoxide as a preservative in tissue sectioning.

The use of a percutaneous penetrant system where the lower aliphatic sulfoxide is less than 25 percent is not adequate to penetrate tissues having a higher density concentration. Contrariwise, percutaneous penetrant systems where the lower aliphatic sulfoxide exceeds 50 percent, have been found to cause significant adverse reactions or systems unjustifiedly relying upon the alleged miraculous qualities of the penetrant itself, rather than the active ingredient. When treating intra-muscular and intra-articular discomfort, a significant balance must be obtained between the concentration of the penetrant serving as the carrier and the anti-inflammatory agent being transported by the carrier percutaneously. Therefore, the need exists for a therapeutic composition which has sufficient penetrant to rapidly carry the active anti-inflammatory agent percutaneously, while not exceeding such concentrations as to mask and diminish the effectiveness of those anti-inflammatory agents. The need further exists to distinguish the proper use of lower aliphatic sulfoxides as a cutaneous penetrant, rather than serving as an active ingredient in the system.

DISCLOSURE OF INVENTION

Therefore, it is an object of the invention to provide a therapeutic composition for the relief of intra-articular and intra-muscular discomfort, wherein the penetrant concentration exceeds 25 percent, but remains less than 50 percent of the total concentration of the composition.

Another object of the invention is to provide a therapeutic composition for the relief of intra-articular and intra-muscular discomfort, wherein the penetrant serves in an absorbent carrier function for physiologically active glucocorticoidal agents.

It is another object of the invention to provide a therapeutic composition, as above, wherein a topical anesthetic compound is applied to the cutaneous surface for the diminished sensory recognition of discomfort within the articular and the muscular areas.

Still another object of the invention is to provide a method for the treatment of intra-articular and intra-muscular discomfort wherein a therapeutic composition, as above, is supplied to the cutaneous surface of the affected area.

Moreover, it is an object of the invention to provide a method for the treatment of intra-articular and intra-muscular discomfort, as above, wherein the therapeutic composition reduces inflammation of the discomforted areas.

It is yet another object of the invention to provide a therapeutic composition and a method for application of the same, as above, wherein the relief is administered percutaneously for direct, controlled, and immediate relief.

These objects, and other objects of the invention which will become more apparent as the detailed description of the best mode for carrying out the invention proceeds, are achieved by: a therapeutic composition for the relief of intra-articular and intra-muscular discomfort, comprising: (a) from about 25 to about 50 parts of a percutaneous penetrant selected from sulfoxides having the following formula:

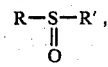

$$R-\underset{\underset{O}{\|}}{S}-R',$$

where R and R' are aliphatic hydrocarbon radicals having from 1 to 5 carbon atoms and may be the same group; (b) from about 0.25 to about 0.75 parts of a topical anesthetic compound; and (c) from about 0.005 to about 0.10 parts of at least one physiologically active glucocorticoidal agent.

The objects of the invention are also achieved by a method for the treatment of intra-articular and intra-muscular discomfort comprising: (a) heating the cutaneous surface over the discomforted intra-articular and intra-muscular areas for a few minutes; and (b) applying a topical application of a therapeutic composition into said cutaneous surface; said therapeutic composition comprising: (a) from about 25 to about 50 parts of a percutaneous penetrant selected from sulfoxides having the following formula:

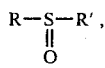

where R and R' are aliphatic hydrocarbon radicals having from 1 to 5 carbon atoms and may be the same radicals; (b) from about 0.25 to about 0.75 parts of a topical anesthetic compound; and (c) from about 0.005 to about 0.10 parts of at least one physiologically active glucocorticoidal agent.

BEST MODE FOR CARRYING OUT THE INVENTION

The use of lower aliphatic sulfoxides, and particularly dimethyl sulfoxide, as a therapeutic agent or carrier for other therapeutic agents has been repeatedly examined by the United States Food and Drug Administration. Claims that the dimethyl sulfoxide (DMSO) serves as a therapeutic agent for the relief of pain are publically announced without specific approval by that Federal agency and amidst scientific controversy. Advocates discussing the use of DMSO as a penetrant carrier for other chemicals are divided into two specific schools of thought: those which advocate the use of the penetrant in concentrations less than 25 percent of the total composition, and those which advocate the concentration greater than 50 percent of the total composition. It has been found by this inventor that the optimal percentage of lower aliphatic sulfoxides to be used as a penetrant and carrier for other active ingredients is between the range of 25 percent and 50 percent of the total composition of the therapeutic compound.

Whenever a concentration greater than 50 percent is employed using a lower aliphatic sulfoxide, and particularly DMSO, the patient experiences a side reaction of a garlic taste in the oral cavity. A test with a percentage of DMSO greater than 50 percent has indicated that the therapeutic action of the composition is not enhanced while the concentration of the DMSO is needlessly high.

Whenever the concentration of the lower aliphatic sulfoxide, and particularly DMSO, is less than 25 percent of the total composition, it has been found that the penetrating capabilities of the entire therapeutic composition is less effective than desired for high-density intra-muscular and intra-articular areas. Consequently, the preferred range has been found to be between 25 percent and 50 percent of the total therapeutic composition.

Relief of intra-muscular and intra-articular discomfort must generally employ an anti-inflammatory agent to relieve pain and swelling of the discomforted areas. Once again, it has been found that these anti-inflammatory agents are most effective when the concentration of the lower aliphatic sulfoxide is between 25 and 50 percent of the total composition. The therapeutic composition may utilize any number of anti-inflammatory agents or any combinations of anti-inflammatory agents sufficient to satisfy the particular articular or muscular treatment desired.

The use of anti-inflammatory agents through injection into the joint has been found to be detrimental to the therapy sought. Injections of anti-inflammatory agents may, within the joint, recrystalize causing synovitis. Percutaneous penetration does not lead to recrystallization of the anti-inflammatory agent.

The anti-inflammatory agents of the present invention are classified as physiologically active glucocorticoidal agents, those adrenal cortical steroids which serve to reduce the inflammation. In the present invention, it has been found that a percentage from about 0.005 to about 0.10 percent of the total therapeutic composition should comprise at least one physiologically active glucocorticoidal agent. Preferably, the concentration is about 0.025 percent of the total therapeutic composition.

Physiologically active glucocorticoidal agents include the following natural and synthesized steroids: adrenocorticotropin hormone (ACTH), cortisone, hydrocortisone, prednisone, prednisolone, triaminolone, methyl prednisolone, meprednisone, paramethasone, fluprednisolone, dexamethasone, and betamethasone. Refinement of the particular glucocorticoidal agent to be used with the treatment of a specific articular or intra-muscular discomfort depends upon the discomfort involved. Glucocorticoidal agents are commonly employed for various rheumatic conditions, including, post-traumatic osteoarthritis, synovitis of osteoarthritis, rheumatoid arthritis, acute and subacute bursitis, epicondylitis, acute nonspecific tenosynovitis, acute gouty arthritis, psoriatic arthritis, and ankylosing spondylitis. Typical collagen diseases which glucocorticoidal agents are employed include systemic lupus erythemoatosus, systemic dermatomysitis, and acute rheumatic carditis.

These anti-inflammatory agents prevent damage to joint collagen and bone tissues as caused by abnormal production of collagenase and enzymes in the synovial fluid. Sybovial cells release latent collagenase which remains latent unless activated by an active enzyme. Rheumatoid cells converts inactive plasminogen into active plasmin enzyme. This latter enzyme activates the latent collagenase into active collagenase, which when in the synovial fluid, attacks the adjacent collagen and bone tissues during joint movement. The anti-inflammatory agents, even in a low concentration, inhibit the production of plasminogen and the converting substance in the rheumatoid cells, thereby maintaining collagenase in its latent form. These anti-inflammatory agents also assist in maintaining the immune processes within the joints themselves.

In addition to the lower aliphatic sulfoxide and at least one physiologically active glucocorticoidal agent, the therapeutic composition of the present invention also includes from about 0.25 to about 0.75 percent of a topical anesthetic compound. The topical anesthetic compound may include any compound known to those skilled in the art to anesthetize the cutaneous surface of the patient. Topical anesthetic compounds include lidocaine, tetracaine, dibucaine, pramoxire HCl, cyclomethycaine sulfate, dimethisoquine HCl, ethyl aminobenzoate (benzocaine), lidocaine HCl, diperodon, butamben picrate, tetracaine HCl, dyclonine HCl, and hexylcaine HCl. The topical anesthetic compound relieves the cutaneous surface of discomfort when the therapeutic composition is applied and the physiologically active glucocorticoidal agent and the percutaneous penetrant are percutaneously absorbed.

The surface area of the skin over the affected joint, bone, or muscle usually have a number of trigger points associated with myofascial and visceral pains. Brief intense stimulation of trigger points frequently produces prolonged relief of pain. It is well known that a short-acting local anesthetic stimulates these trigger points to create a prolonged, perhaps permanent, relief from myofascial and visceral pain. This intense stimulation, called hyperstimulation, is necessary in the therapeutic composition of the present invention to relieve pain while the glucocorticoidal agents block activation of collagenase. The synergistic combination of analgesia and anti-inflammatory medication is only possible with cutaneous application having percutaneous penetrants therein.

Because of the continuing controversy surrounding the use of lower aliphatic sulfoxides as claimed active ingredients and as known penetrants, testing of the therapeutic composition of the present invention was conducted under strict control of availability of material. The lower aliphatic sulfoxides of the present invention have the following formula:

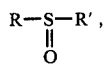

where R and R' are aliphatic hydrocarbon radicals having from 1 to 5 carbon atoms and may be the same radicals. Preferably, the percutaneous penetrant of the present invention is dimethyl sulfoxide where R and R' are both methyl groups.

The method of treatment for the intra-articular and intra-muscular discomfort of patients comprises heating the cutaneous surface over the discomforted intra-articular and intra-muscular areas for a few minutes with a warm substance, such as a hot towel or other similar method known to those skilled in the art. If moist heat is used, the cutaneous surface should be dried before applying the topical application of the therapeutic composition of the present invention onto the cutaneous surface. This second step should be enhanced by a gentle rubbing of the surface to enhance the functions of the anesthetic compound and to permit penetration of the percutaneous penetrant and the physiologically active glucocorticoidal agent. This treatment should be repeated daily or more often until the discomfort in the articular and muscular areas subsides.

The percutaneous penetrant, the topical anesthetic compound and at least one physiologically active glucocorticoidal agent may be mixed with a unibase ointment solvent, commonly known to those skilled in the art. This unibase ointment is water soluble and frequently employed as a substrate within which the active ingredients of any medication may be used. The unibase ointment comprises glycerine, sodium laurel sulfate, sodium citrate, and propyl paraben. The penetrant, anesthetic compound, and glucocorticoidal agents may be mixed directly into about 100 parts of the unibase ointment solvent, such that the sulfoxide penetrant comprises from about 25 to about 50 parts, the topical anesthetic compound comprises from about 0.25 to about 0.75 parts, and the physiologically active glucocorticoidal agent comprises from about 0.005 to about 0.10 parts. Preferably, the penetrant comprises 40 parts, the topical anesthetic compound comprises 0.50 parts, and the glucocorticoidal agent comprises about 0.025 parts of the therapeutic composition. The relative concentrations expressed in parts or percentages of these components of the composition do not reflect the solvents or solutions in which they are typically commercially available.

INDUSTRIAL APPLICABILITY

The administration of a therapeutic composition of the present invention has achieved significant utility by reducing conditions of discomfort resulting from bursitis, arthritis, and other diseases. The following cases demonstrate the unexpected recovery of patients following treatment with the therapeutic composition of the present invention.

The therapeutic composition was prepared according to the following method. Into about 454 grams of unibase ointment was mixed about 192 milliliters of dimethyl sulfoxide 100 percent solution to create about a 40 percent DMSO penetration concentration. Next, approximately 48 milliliters of a 5 percent topical cyclaine solution was added to the unibase composition to create a 0.5 percent concentration of the topical anesthetic compound. The 5 percent topical Cyclaine solution is commercially available from Merck Sharp Dohme, which serves as a tradename for hexylcaine HCl. To that composition was added two physiologically active glucocorticoidal agents, the first being approximately 2½ milliliters of ACTH (40 units/5 ml) or 100 units of ACTH, a commercially available quantity from Parke-Davis Company. Finally, approximately 48 milliliters of Decadron elixir was added to the therapeutic composition as another glucocorticoidal agent. Decadron elixir is a commercial quantity available from Merck Sharp Dohme, as a tradename for dexamethasone. Each milliliter of elixir has 0.1 milligrams of dexamethasone, and the therapeutic composition, therefore, contains 0.000105 percent of the total therapeutic composition.

As an equivalent to 100 units of ACTH, it has been found that approximately 2½ milliliters of Depomedrol (40 mg/ml) may be a physiologically active glucocorticoidal agent. Depomedrol (40 mg/ml) is a commercially available quantity available from the UpJohn Company as a tradename for methylprednisolone acetate. This Depomedrol contains 40 milligrams of methylprednisolone acetate per milliliter of solution, which creates a concentration of glucocorticoidal agent of about 0.022 percent of the therapeutic composition.

The following cases illustrate the direct, controlled, and immediate therapeutic effect of the therapeutic composition for patients having a variety of discomforts.

CASE 1

The patient is a male, aged 59, who has had therapy for several months on his right shoulder under the care of several doctors with no significant improvement. Upon physical examination, the chief complaints are severe pain in the right shoulder with the inability to raise or extend the arm. The pressure point area of the right shoulder is tender upon pressure, and the orthrodiagram shoulder temperature indicates a chronic pain. Laboratory tests indicate CBC-normal, WBC-normal, RA factor-negative, BUN ground range blood sugar-normal limits. The diagnosis is acute and chronic bursitis of the right shoulder.

Therapy was begun with the therapeutic composition, (ACTH formulation), used topically to the shoulder area and muscles. Daily treatment included the application of hot towels for five minutes to the area, a drying of the area, and the application of the therapeutic composition with a gentle rubbing of the ointment into the skin. After approximately three weeks of daily treatment, pain has left the right shoulder and complete use of the arm, including raising and rotating the right arm, was obtained without discomfort.

CASE 2

The patient is a male, aged 52 who has been treated by several doctors with intra-articular injections. The physical examination showed chief complaints to be severe pain in right shoulder area and pain radiating down the neck and arm. The arm could not be elevated. Laboratory tests indicated CBC-normal, WBC 8,150, blood sugar-100 milligrams, BUN-81 milligrams, normal range, cholesterol-284. The diagnosis is chronic bursitis of the right shoulder.

Therapy was begun with daily treatments of the therapeutic composition (ACTH formulation) and hot towels as described with Case 1. Daily treatment continues for approximately three weeks. The present condition finds no pain, a relief of tenderness in the right shoulder, and the elevation and extension of the right arm, performed without pain. Further, no pressure point pain was found.

CASE 3

The patient is a female, aged 57 who had visited several doctors with no satisfactory results. Upon physical examination, the chief complaints were the inability to close the fingers to make a fist for both hands. The tenderness in both hands was located in the tendons, which prevented the patient from tying shoelaces or other objects. Laboratory results indicated CBC-adequate, blood sugar-114 milligrams, BUN-122 (normal range), cholesterol-224 milligrams, triglycerides-elevated, latex test-negative. The diagnosis was acute tinoocysnomitis of ligaments of both hands.

Therapy was initiated with daily treatment of hot towels applied to the fingers and wrists on the dorium of the hands for approximately five minutes, a drying of the heated area, and the application and gentle rubbing of the therapeutic composition of the present invention (ACTH formulation). While the treatment continued for several weeks, after one week, the patient was able to tie her shoelaces and make a fist in both hands. After a few weeks, all pain was relieved and the patient was eventually able to return to work and perform normal manipulative duties.

CASE 4

The patient is a female, aged 94. Upon examination, the chief complaints were the inability by the patient to walk without pain in her hip joints and knee joints. The laboratory results indicate WBC-7800, blood sugar-104, BUN-126 (normal), cholesterol-225 (elevated), latex-negative, SED. rate-elevated. The diagnosis is inflammatory arthritis of the knees and hip joints.

Therapy was begun with daily treatment by the application of hot towels to both of the knees and the hip joints for approximately five minutes. These areas were dried and then the application of the therapeutic composition (ACTH formulation) was gently applied to these areas. Within one and one-half weeks the patient was free of pain and able to walk without any discomfort.

CASE 5

The patient is a male, aged 62. A physical examination finds the chief complaints to be pain in both knees and hip joints. Laboratory results indicate WBC-6600, HB-16-2, SED. rate-26, blood sugar-79, BUN-9.8, cholesterol-257, triglycerides-elevated, antigen check of B13 and B17-presence showing. The diagnosis is psoriatic arthritis in both knees and hip joints.

Therapy was initiated with daily treatments to both knees and hip joints, according to the methods described above. After daily treatment, lasting approximately two weeks, the knees and hip joints were free of pain, and improved motion of the joints obtained without pain.

CASE 6

The patient is a female, aged 56, who has visited several doctors over a period of years for treatment of arthritis. The results have been unsatisfactory. Upon physical examination, the chief complaints are severe pain in the knees, hip joints, and neck area. Laboratory results indicate WBC-13650, HB-15.7, blood sugar-89, BUN-8.6, cholesterol-200, triglycerides-125, SED. rate-4 millimeters (9-20 normal), RA latex test-negative. The diagnosis is infectious arthritis of the knees and hips and neck area.

Therapy was initiated with the application of hot towels to the area for approximately 5 minutes, drying of the area, and a gentle application of the therapeutic composition (ACTH formuation). This daily treatment continued for several weeks. All symptoms of pain in the affected areas disappeared. The movement of joints improved and the WBC count returned to the normal range of 6800.

As the case studies indicate, the therapeutic composition provides a direct, controlled, and immediate relief to patients who have a variety of intra-articular and intra-muscular discomforts. These representative cases further demonstrate the penetrant capabilities of the active ingredients when the therapeutic composition has approximately 40 percent of a lower aliphatic sulfoxide, particularly dimethyl sulfoxide. The action of the anesthetic compound on the trigger points for myofascial and visceral pain and the action of the glucocorticoidal agents to reduce inflammation and inhibit plasminogen production is a synergistic combination in the therapeutic composition to satisfy the medicinal needs of those patients.

While in accordance with the patent statutes, a best mode for carrying out the invention has been disclosed, it is to be understood that the invention is not limited thereto or thereby. Consequently, for an understanding of the invention, reference is had to the following claims.

What is claimed is:

1. A therapeutic composition for the relief of intra-articular and intra-muscular discomfort beneath cutaneous surfaces, comprising:

(a) from about 25 to less than 50 parts by weight of a percutaneous penetrant selected from sulfoxides having the following formula:

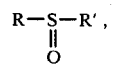

where R and R' are aliphatic hydrocarbon radicals having from 1 to 5 carbon atoms and may be the same group;
(b) from about 0.25 to about 0.75 parts by weight of a topical anesthetic compound; and
(c) from about 0.005 to about 0.10 parts by weight of at least one physiologically active glucocorticoidal agent selected from the group consisting of: adrenocoricotropin hormone (ACTH), cortisone, hydrocortisone, prednisone, prednisolone, triaminolone, methyl prednisolone, meprednisone, paramethasone, fluprednisolone, dexamethasone, and betamethasone.

2. A therapeutic composition, according to claim 1, wherein the composition further comprises about 100 parts of a unibase ointment solvent, said solvent comprising glycerine, sodium laurel sulfate, sodium citrate, and propyl paraben.

3. A therapeutic composition, according to claim 1, wherein there are two physiologically active glucocorticoidal agents in the therapeutic composition, and wherein the amount of said penetrant is about 40 parts by weight.

4. A therapeutic composition, according to claim 3, wherein said physiologically active glucocorticoidal agents comprise from about 0.00005 parts to about 0.099 parts of dexamethasone, and from about 0.001 parts to about 0.099 parts of methyl prednisolone.

5. A therapeutic composition, according to claim 4, wherein said physiologically active glucocorticoidal agent comprise about 0.00011 parts of dexamethasone and about 0.022 parts of methyl prednisolone.

6. A therapeutic composition, according to claim 3, wherein said physiologically active glucocorticoidal agent comprises from about 0.00005 parts to about 0.099 parts of dexamethasone and from about 0.001 parts to about 0.099 parts of adreno corticotropin hormone.

7. A therapeutic composition, according to claim 6, wherein said physiologically active glucocorticoidal agent comprise about 0.00011 parts of dexamethasone and about 0.022 parts of methyl prednisolone.

8. A therapeutic composition, according to claim 1, wherein said percutaneous penetrant comprises dimethyl sulfoxide.

9. A method for the treatment of intra-articular and intra-muscular discomfort beneath a cutaneous surface, comprising:
(a) heating the cutaneous surface over the discomforted intra-articular and intra-muscular areas for a few minutes;
(b) applying a topical application of a therapeutic composition into said cutaneous surface;
said therapeutic composition comprising:
(a) from about 25 to about 50 parts of a percutaneous penetrant selected from sulfoxides having the following formula:

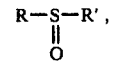

where R and R' are aliphatic hydrocarbon radicals having from 1 to 5 carbon atoms and may be the same radical;
(b) from about 0.25 to about 0.75 parts of a topical anesthetic compound; and
(c) from about 0.005 to about 0.10 parts of at least one physiologically active glucocorticoidal agent selected from the group consisting of adrenocorticotropin hormone (ACTH), cortisone, hydrocortisone, prednisone, prednisolone, triaminolone, methyl prednisolone, meprednisone, paramethasone, fluprednisolone, dexamethasone, and betamethasone.

10. A method for the treatment of intra-articular and intra-muscular discomfort, according to claim 9 wherein the composition further comprises about 100 parts of a unibase ointment solvent, said solvent comprising glycerine, sodium laurel sulfate, sodium citrate, and propyl paraben.

11. A method for the treatment of intra-articular and intra-muscular discomfort, according to claim 9, wherein there are two physiologically active glucocorticoidal agents in the therapeutic composition.

12. A method for the treatment of intra-articular and intra-muscular discomfort, according to claim 9, wherein said percutaneous penetrant comprises dimethyl sulfoxide.

13. A therapeutic composition, according to claim 3, wherein said topical anesthetic compound is selected from the group consisting of lidocaine, tetracaine, dibucaine, pramoxire HCl, cyclomethycaine sulfate, dimethisoquine HCl, ethyl aminobenzoate (benzocaine), lidocaine HCl, diperodon, butamben picrate, tetracaine HCl, dyclonine HCl, hexylcaine HCl, and combinations thereof.

14. A method for the treatment of intra-articular and intra-muscular discomfort according to claim 11, wherein said topical anesthetic is selected from the group consisting of lidocaine, tetracaine, dibucaine, pramoxire HCl, cyclomethycaine sulfate, dimethisoquine HCl, ethyl aminobenzoate (benzocaine), lidocaine HCl, diperodon, butamben picrate, tetracaine HCl, dyclonine HCl, hexylcaine HCl, and combinations thereof.

* * * * *